United States Patent
Fukuda et al.

(10) Patent No.: US 7,531,510 B2
(45) Date of Patent: May 12, 2009

(54) METHODS OF RECRUITING FIBROBLASTS BY ADMINISTERING G-CSF

(75) Inventors: Keiichi Fukuda, Shinjuk-ku (JP); Jun Fujita, Shinjuku-ku (JP)

(73) Assignees: Keio University, Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 138 days.

(21) Appl. No.: 10/577,241

(22) PCT Filed: Oct. 27, 2004

(86) PCT No.: PCT/JP2004/016290

§ 371 (c)(1),
(2), (4) Date: Apr. 26, 2006

(87) PCT Pub. No.: WO2005/039621

PCT Pub. Date: May 6, 2005

(65) Prior Publication Data

US 2007/0081970 A1    Apr. 12, 2007

(30) Foreign Application Priority Data

Oct. 27, 2003 (JP) .............................. 2003-366480
Feb. 13, 2004 (JP) .............................. 2004-036613

(51) Int. Cl.
*A61K 38/00* (2006.01)
*A61K 45/00* (2006.01)
(52) U.S. Cl. ........................................ 514/12; 424/85.1
(58) Field of Classification Search ....................... None
See application file for complete search history.

(56) References Cited

U.S. PATENT DOCUMENTS 7,220,407 B2 * 5/2007 Mehta et al. ................ 424/85.1
7,294,334 B1 * 11/2007 Michal et al. ............... 424/93.7

OTHER PUBLICATIONS

Orlic D et al. PNAS 98(18):10344-10349, 2001.*

* cited by examiner

*Primary Examiner*—Robert Landsman
(74) *Attorney, Agent, or Firm*—Browdy and Neimark, P.L.L.C.

(57) ABSTRACT

The object of the present invention is to achieve simple recruitment of fibroblasts into wounded tissues and engraftment of the fibroblasts in the wounded tissues, thereby healing the wounds without requiring fibroblast transplantation. Upon G-CSF administration, fibroblasts migrate into myocardial infarct lesions and prevent a reduction in cardiac function, thus alleviating cardiac remodeling.

11 Claims, 21 Drawing Sheets

Green: GFP
Blue: DAPI (60 days after BM transplantation)

↕ Left venticular end-diastolic diamenter

↑↓ Left venticular end-systolic diamenter

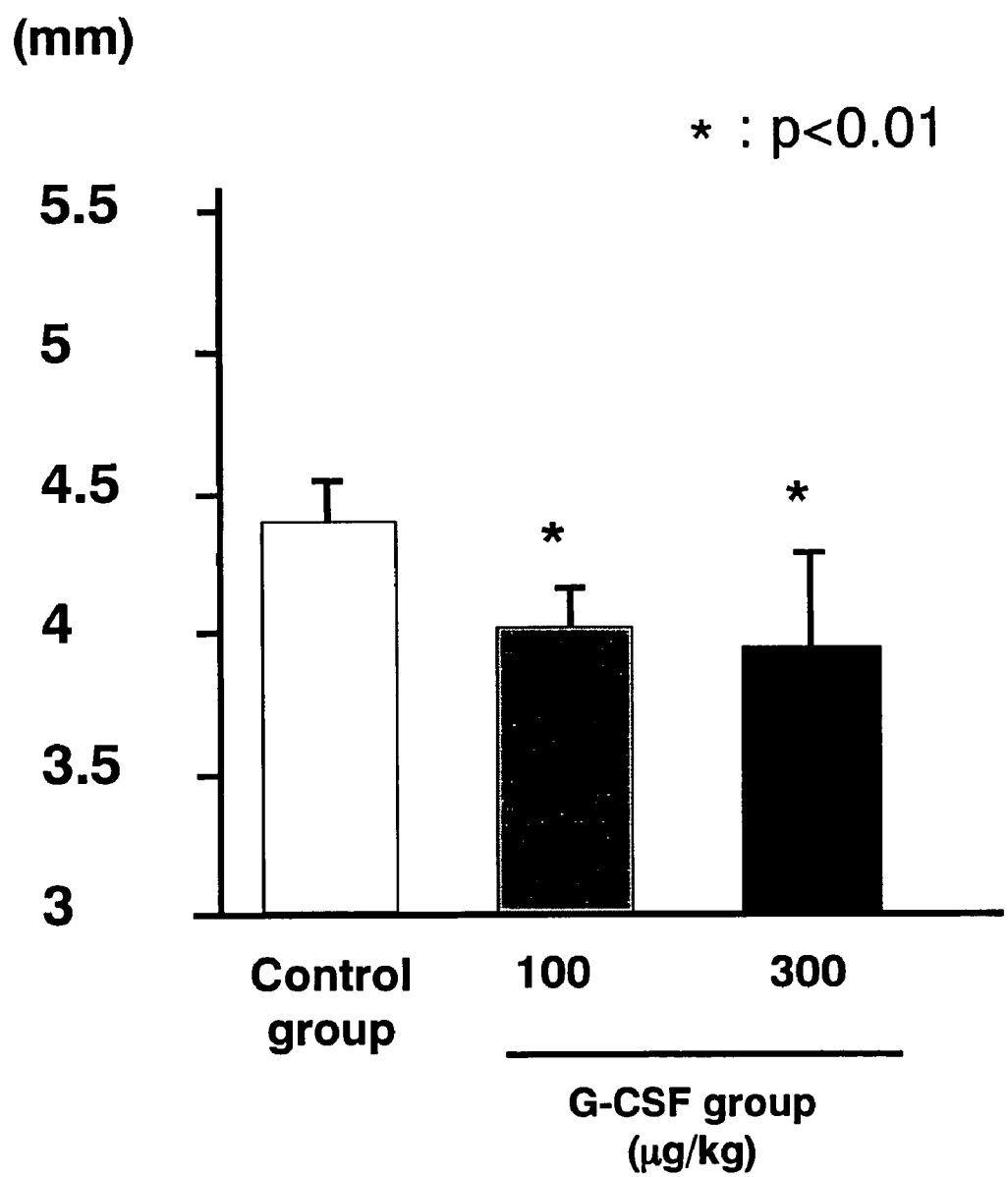

Figure 7(a)
Azan staining
Control group
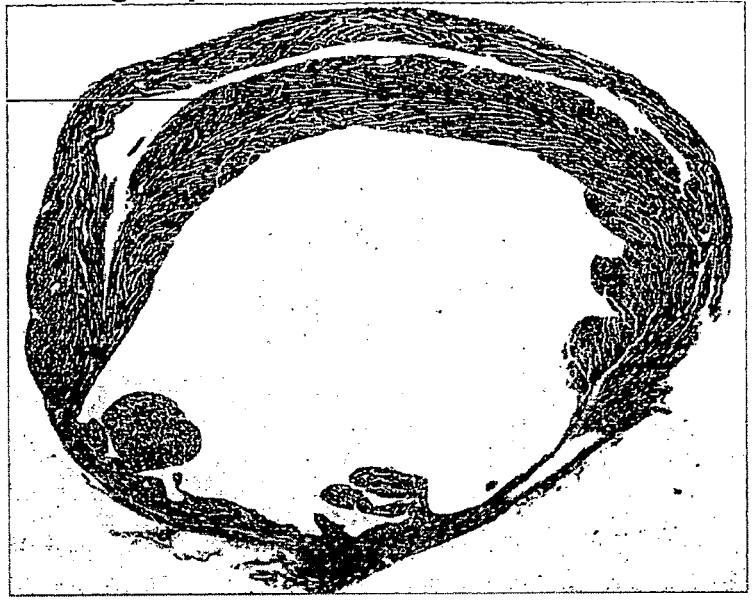
G-CSF group
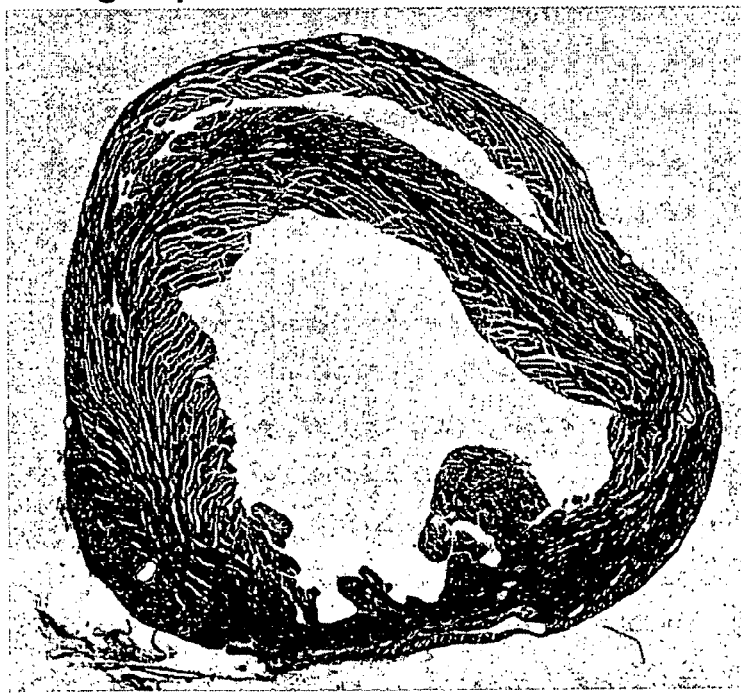

Figure 7(b)
Azan staining
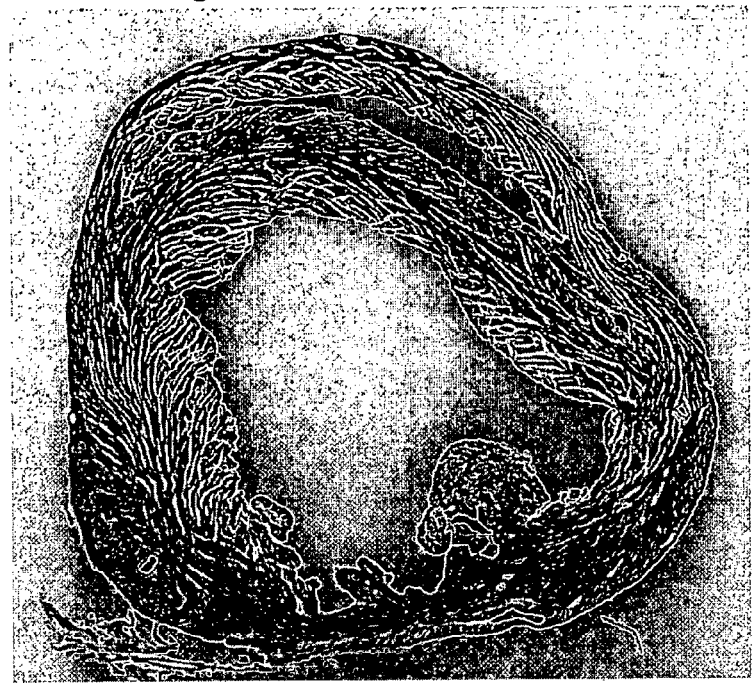
Confocal laser scanning microscope
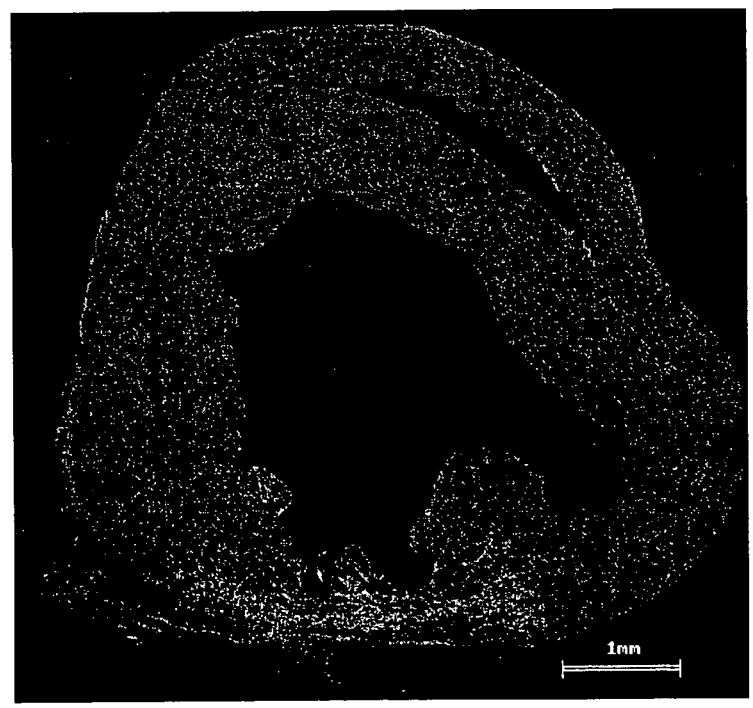
60 days after myocardial infarction

Figure 10
Anti-α-smooth muscle
actin antibody
GFP
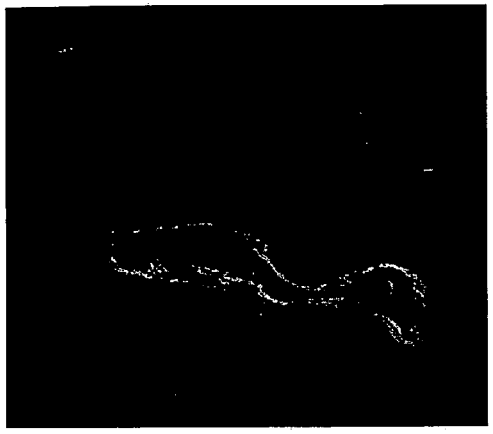
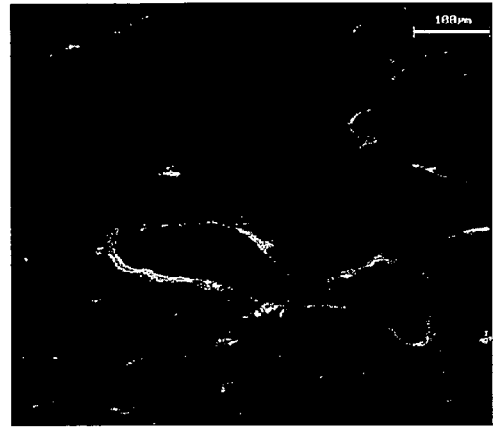
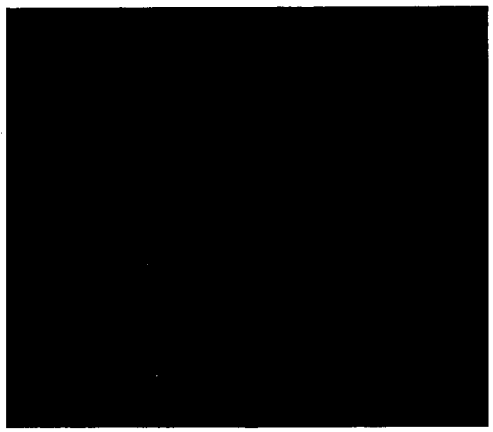
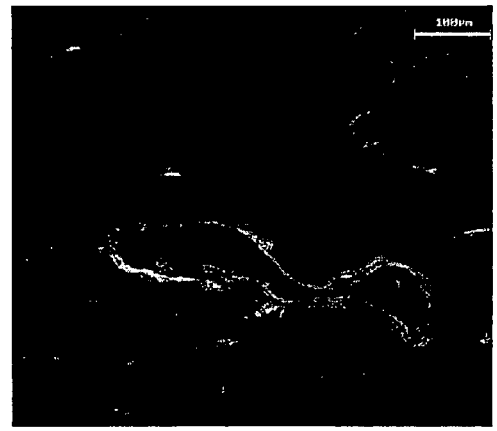
DAPI
Green: GFP
Red: Anti-α-smooth muscle actin antibody
Blue: DAPI Green: GFP
Red: Anti-vWF antibody
Blue: DAPI

**Green: GFP
Red: Anti-myocardial actinin antibody
Blue: DAPI**

Green: GFP
Red: Anti-myocardial actinin antibody
Blue: DAPI

■ Myocardial cells

▨ Smooth muscle cells

■ Vascular endothelial cells

☐ Fibroblast-like cells

Green: GFP
Red: Anti-vimentin antibody
Blue: DAPI

Green: GFP
Red: Anti-myocardial actinin antibody
Blue: DAPI

METHODS OF RECRUITING FIBROBLASTS BY ADMINISTERING G-CSF

TECHNICAL FIELD

The present invention relates to a substance for recruiting fibroblast, which comprises granulocyte colony-stimulating factor (G-CSF) as an active ingredient. The present invention also relates to a substance for engrafting fibroblast, which comprises G-CSF as an active ingredient. The present invention further relates to a therapeutic agent for healing wound, which comprises G-CSF as an active ingredient.

BACKGROUND ART

Human G-CSF is a hematopoietic factor found as a differentiation-inducing factor for hematopoietic stem cells of the granulocytic lineage and is clinically used as a therapeutic agent for neutropenia following bone marrow transplantation or cancer chemotherapy because it promotes in vivo hematopoiesis of neutrophils. In addition to this action, human G-CSF acts on stem cells to stimulate their differentiation and proliferation, and also recruits stem cells from the bone marrow into the peripheral blood. Based on the latter action, in fact, transplantation of the peripheral blood hematopoietic stem cells recruited by human G-CSF, i.e., peripheral blood stem cell transplantation is performed in a clinical setting, with the aim of facilitating hematopoietic recovery in cancer patients after intensive chemotherapy.

DISCLOSURE OF THE INVENTION

The object of the present invention is to achieve simple recruitment of fibroblasts into wounded tissues and engraftment of the fibroblasts in the wounded tissues, thereby healing the wounds without requiring fibroblast transplantation.

The inventors of the present invention have examined the regeneration of wounded tissues following myocardial infarction. As a result, the inventors have found that upon G-CSF administration, fibroblasts migrate into myocardial infarct lesions and prevent a reduction in cardiac function, thus alleviating cardiac remodeling. This finding led to the completion of the present invention.

Namely, the present invention provides a substance for recruiting fibroblast, which comprises granulocyte colony-stimulating factor (G-CSF) as an active ingredient.

The present invention also provides a substance for engrafting fibroblast in a heart after the onset of heart disease, which comprises G-CSF as an active ingredient.

The present invention also provides a therapeutic agent for healing wound, which comprises G-CSF as an active ingredient.

The present invention further provides a method for recruiting fibroblast, which comprises administering an effective amount of G-CSF.

The present invention also provides a method for engrafting fibroblast in a heart after the onset of heart disease, which comprises administering an effective amount of G-CSF.

The present invention also provides a method for healing wound, which comprises administering an effective amount of G-CSF.

When G-CSF was administered after myocardial infarction, a large number of bone marrow cell-derived myocardial cells were observed in infarct lesions. On the other hand, a nearly 10-fold higher number of fibroblasts were also observed. This indicates that G-CSF administration induced migration of various stem cell-derived cells from the bone marrow into infarct lesions, allowed regeneration of the infarct lesions and prevented remodeling following myocardial infarction. G-CSF administration appears to facilitate wound healing and to alleviate remodeling through not only infiltration of many leukocytes during the acute stage, but also migration of fibroblasts into infarct lesions during the chronic stage (60 days after infarction). It has been reported that when fibroblasts were transplanted into infarct lesions following myocardial infarction, remodeling of the infarct lesions could be prevented (Hutcheson K A, Atkins B Z, Hueman M T, Hopkins M B, Glower D D, Taylor D A, Transplant. 9, 2000, 359-368). In the present invention, G-CSF can be administered after myocardial infarction so as to induce migration of fibroblasts from the bone marrow. Thus, the present invention can prevent remodeling of infarct lesions without requiring fibroblast transplantation, and hence is very useful for clinical applications.

This fact also means that G-CSF can be clinically applied during various wound healing processes for trauma and so on, in addition to myocardial infarction. Namely, when G-CSF is administered during the wound healing process, not only early infiltration of granulocytes, but also supply of fibroblasts can be caused to accelerate wound healing, thus resulting in a healed tissue that is much stronger. It has previously been considered that G-CSF administration during wound healing causes infiltration of many granulocytes and leads to tissue destruction (Romson, J L, Hook B G, Kunkel S L, Abrams G D, Schork M A, Lucchesi B R, Circulation 67(5), 1983, 1016-1023). However, in the present invention, G-CSF administration allows a stronger healing of wounded sites.

BRIEF DESCRIPTION OF DRAWINGS

FIG. 6 is a graph showing the effect of G-CSF administration on left ventricular end-diastolic diameter at 60 days after creation of myocardial infarction. From the left, the bars show the results of the normal group, the G-CSF group (100 µg/kg) and the G-CSF group (300 µg/kg), respectively.

FIG. 7(a) shows Azan-stained, short-axis cross-sections of the heart left ventricles from the control group (left panel) and the G-CSF group (right panel) at 60 days after creation of myocardial infarction. Areas stained in red represent muscle fibers, while areas stained in blue represent collagen fibers.

FIG. 7(b) shows a short-axis cross-section of the heart left ventricle from the G-CSF group at 60 days after creation of myocardial infarction, as analyzed by Azan staining (left panel) and under a confocal laser scanning microscope (right panel).

FIG. 10 shows confocal laser scanning microscopic photographs of a single myocardial infarct lesion immunostained with anti-α-smooth muscle actin antibody. Green signals represent GFP-positive cells, blue signals represent DAPI-stained nuclei, and red signals represent α-smooth muscle actin.

BEST MODE FOR CARRYING OUT THE INVENTION

Figure 1:
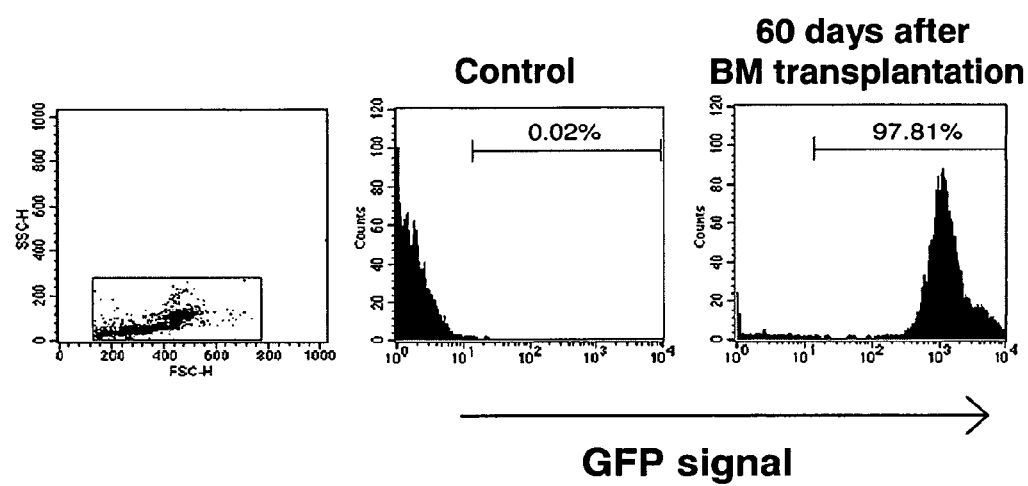
FIG. 1 shows the results of FACS analysis performed on peripheral blood nucleated cells at 60 days after bone marrow transplantation.

The present invention relates to a substance for recruiting fibroblast, which comprises G-CSF as an active ingredient. There is no particular limitation on the site where fibroblasts are recruited. For example, in a case where there is a wounded tissue, fibroblasts can be recruited into the wounded tissue by G-CSF administration.

As used herein, the term "wound" or "wounded" refers to damage or injury to body tissues. Examples include damage or injury to internal tissues or organs (e.g., heart, lung, kidney, intestine, liver, tendon), as well as trauma to the skin, etc. As specific examples of wounded tissues, myocardial infarcted hearts can be preferably presented.

In general, fibroblasts are unique to connective tissue and have oval nuclei and spindle-shaped protoplasm, characterized by good development of rough endoplasmic reticulum and Golgi apparatus. Moreover, fibroblasts also include mesenchymal lineage cells which are found in many organs and play a role in parenchymal filling. Fibroblasts generally have the ability to produce large amounts of interstitial substances (e.g., collagen, fibronectin, mucopolysaccharides) in the body. Fibroblast recruitment into wounded tissues enables the facilitation of wound healing.

The present invention also relates to a substance for engrafting fibroblast in a heart after the onset of heart disease, which comprises G-CSF as an active ingredient.

Specific examples of heart diseases include ischemic heart diseases (e.g., myocardial infarction) and myocardial diseases (e.g., cardiomyopathy). For example, G-CSF administration after myocardial infarction enables fibroblasts engraftment into myocardial infarct lesions.

The present invention further relates to a therapeutic agent for healing wound, which comprises G-CSF as an active ingredient.

G-CSF used in the present invention is not limited in any way, but a highly purified one is preferred. Specific examples include mammalian G-CSF, particularly those having substantially the same biological activities as human G-CSF. G-CSF used herein may be of any origin, including those naturally occurring and those produced recombinantly, with recombinantly produced G-CSF being preferred. Such recombinantly produced G-CSF may have the same amino acid sequence as naturally-occurring G-CSF or may comprise deletion, substitution and/or addition of one or more amino acid residues in the amino acid sequence as long as it retains the same biological activities as naturally-occurring G-CSF. Amino acid deletions, substitutions or additions may be accomplished in a manner known to those skilled in the art. For example, those skilled in the art will be able to use site-specific mutagenesis (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; Kunkel, T. A. (1985) Proc. Natl. Acad. Sci. USA. 82, 488-492; Kunkel (1988) Methods Enzymol. 85, 2763-2766) or other techniques to introduce appropriate mutations into the amino acid sequence of G-CSF, thereby preparing a polypeptide functionally equivalent to G-CSF. Likewise, amino acid mutations may also occur in the natural world. In general, amino acid residues to be substituted are preferably replaced with other amino acids in such a manner as to conserve the nature of amino acid side chains. With regard to the nature of amino acid side chains, examples include hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy-containing side chain (S, T, Y), amino acids having a sulfur-containing side chain (C, M), amino acids having a carboxylic acid- or amide-containing side chain (D, N, E, Q), amino acids having a base-containing side chain (R, K, H), and amino acids having an aromatic-containing side chain (H, F, Y, W) (capital letters in parentheses refer to the corresponding amino acids in single-letter notation). It is already known that a polypeptide having an amino acid sequence modified from another amino acid sequence by deletion and/or addition of one or more amino acid residues and/or by their substitution with other amino acids retains the same biological activities as the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

Moreover, in the present invention, G-CSF may be administered as a protein, but it is also possible to administer a gene encoding G-CSF, as in gene therapy. The gene encoding G-CSF is generally administered, for example, as an expression vector containing an expression cassette. The vector is not limited in any way, and either a non-virus or virus vector may be used (e.g., Supplementary Volume of Experimental Medicine, "Experimental Methods for Gene Transfer and Expression Analysis," YODOSHA, 1996). Examples of the vector include a plasmid vector, a virus vector, a phage vector, a cosmid vector and a YAC vector. The expression vector normally includes a regulatory element, such as a promoter. Any method is available for gene transfer, and include, for example, calcium phosphate transfection, lipofection, a method using a liposome, the naked-DNA method, receptor-mediated gene transfer, a method using a gene gun, DEAE-dextran transfection, and a method using a capillary tube. In the present invention, the gene may be directly transferred into the body, or after gene transfer into cells taken up from the body, the cells may be returned into the body.

It is also possible to use fusion proteins between G-CSF and other proteins. To prepare a fusion polypeptide, for example, DNA encoding G-CSF and DNA encoding another protein may be ligated together in-frame, introduced into an expression vector and then expressed in a host. Other proteins to be fused herein with G-CSF are not limited in any way.

Moreover, it is also possible to use chemically modified G-CSF. Examples of chemically modified G-CSF include those modified by structural alteration, addition and/or deletion of sugar chains, as well as those conjugated with a compound such as an inorganic or organic compound (e.g., polyethylene glycol, vitamin B12).

G-CSF used in the present invention may be prepared in any manner, for example, by culturing human tumor cell lines or human G-CSF-producing hybridoma cell lines or by genetically engineered production in E. coli cells, yeast cells, Chinese hamster ovary (CHO) cells, C127 cells, COS cells, myeloma cells, BHK cells, insect cells, etc. G-CSF thus prepared is extracted, isolated and purified in various manners before use. G-CSF used in the present invention is preferably a genetically engineered one, more preferably G-CSF produced in mammalian cells (particularly CHO cells) (e.g., JP 1-44200 B, JP 2-5395 B, JP 62-129298 A, JP 62-132899 A, JP 62-236488 A, JP 64-85098 A).

If necessary, depending on the administration mode and the dosage form, the substances of the present invention for fibroblast recruitment or other purposes may be supplemented as appropriate with a suspending agent, a solubilizing agent, a stabilizing agent, an isotonizing agent, a preservative, an anti-adsorption agent, a surfactant, a diluent, an excipient, a pH adjustor, a soothing agent, a buffer, a sulfur-containing reducing agent, an antioxidant or the like.

Examples of a suspending agent include methylcellulose, Polysorbate 80, hydroxyethylcellulose, gum arabic, powdered tragacanth, carboxymethylcellulose sodium, and polyoxyethylenesorbitan monolaurate.

Examples of a solubilizing agent include polyoxyethylene hydrogenated castor oil, Polysorbate 80, nicotinamide, polyoxyethylenesorbitan monolaurate, Magrogol, and an ethyl ester of castor oil fatty acid.

Examples of a stabilizing agent include Dextran 40, methylcellulose, gelatin, sodium sulfite, and sodium metasulfite.

Examples of an isotonizing agent include D-mannitol and sorbitol.

Examples of a preservative include methyl paraoxybenzoate, ethyl paraoxybenzoate, sorbic acid, phenol, cresol, and chlorocresol.

Examples of an anti-adsorption agent include human serum albumin, lecithin, dextran, ethylene oxide-propylene oxide copolymers, hydroxypropylcellulose, methylcellulose, polyoxyethylene hydrogenated castor oil, and polyethylene glycol.

Examples of a sulfur-containing reducing agent include those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a $C_1$-$C_7$ thioalkanoic acid.

Examples of an antioxidant include erythorbic acid, dibutylhydroxytoluene, butylhydroxyanisole, α-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as ethylenediaminetetraacetic acid disodium salt (EDTA), sodium pyrophosphate and sodium metaphosphate.

Furthermore, the substances of the present invention for fibroblast recruitment or other purposes may comprise other commonly used ingredients, e.g., inorganic salts such as sodium chloride, potassium chloride, calcium chloride, sodium phosphate, potassium phosphate and sodium bicarbonate, as well as organic salts such as sodium citrate, potassium citrate and sodium acetate.

The substances of the present invention for fibroblast recruitment or other purposes may be administered in a dosage form of injections (e.g., subcutaneous, intracutaneous, intramuscular, intravenous or intraperitoneal injections), in any dosage form suitable for transdermal, transmucosal or transnasal administration or in any dosage form suitable for oral administration (e.g., tablets, capsules, granules, solutions, suspensions). The present invention is not limited by the route of administration or dosage form, etc.

In the substances of the present invention for fibroblast recruitment or other purposes which comprises G-CSF as an active ingredient, the dose and frequency of its administration can be determined as appropriate by those skilled in the art by taking into account symptoms of a diseased patient to be treated. In general, G-CSF may be administered at a dose of 0.1 to 500 µg/kg/day per adult, preferably 1 to 50 µg/kg/day per adult, for 1 to 7 days per week. However, the present invention is not limited by the dose of G-CSF. Alternatively, the substances of the present invention for fibroblast recruitment or other purposes may be used in combination with other pharmaceutical agents.

EXAMPLES

Example 1

Whole Bone Marrow Transplantation (1) Creation of Murine Bone Marrow Transplantation Model C57BL/6 mice at 8 to 10 weeks of age (CLEA, Tokyo, Japan) were irradiated once with a lethal dose of total body irradiation (850 cGy) using a $4 \times 10^6$ V linear accelerator and used as recipient mice. Bone marrow crude fractions were collected from the femurs and neck bones of GFP transgenic mice (C57BL/6, 10-12 weeks of age) (Okabe et al., (1997) FEBS. Lett. 407, 313-319), and $5 \times 10^6$ bone marrow cells were transplanted into the recipient mice through their tail veins.

To confirm what percentage of donor-derived GFP-positive bone marrow cells have been engrafted in the bone marrow of the recipients (this percentage being hereinafter referred to as "chimera rate"), peripheral blood nucleated cells obtained at 60 days after bone marrow transplantation were analyzed using a FACS Calibur (Becton Dickinson, San Jose, Calif., USA). FIG. 1 shows the results obtained. In the control mice, GFP expression was not observed in their bone marrow nucleated cells, whereas cells in the bone marrow-transplanted mice were GFP-positive at a rate of 97.8%. The degree of chimera rate is an important index in quantifying donor-derived GFP-positive cells. In this experiment, mice whose chimera rate of peripheral blood cells averaged 95% or more were used as a murine bone marrow transplantation model. This is considered as being able to satisfy the requirement for sufficient quantification and evaluation of the contribution of bone marrow-derived cells to wound healing.

Figure 2:
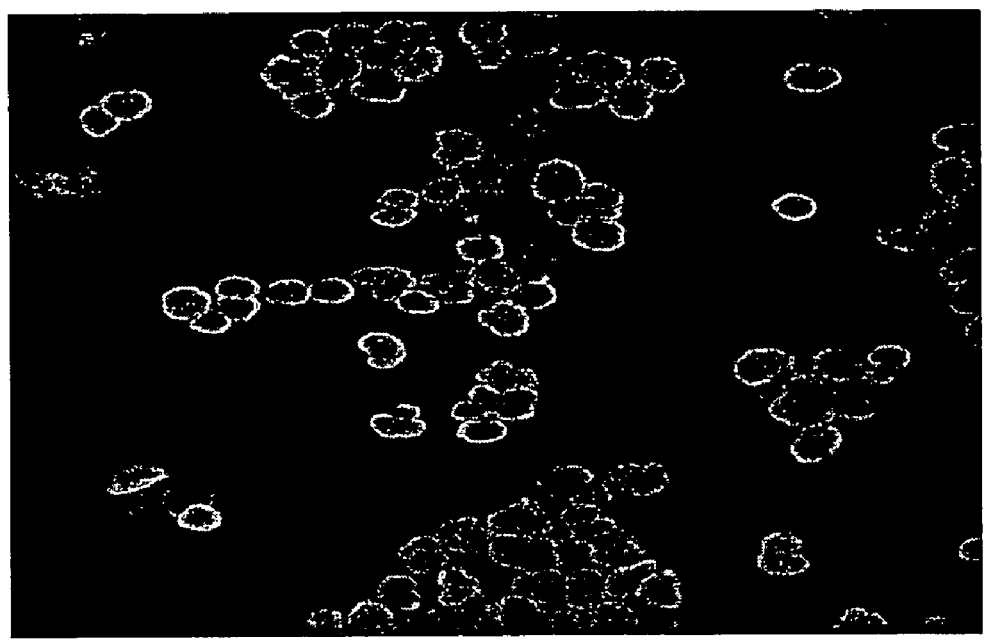
FIG. 2 shows a confocal laser scanning microscopic photograph of a bone marrow cytospin specimen. Green signals represent GFP-positive bone marrow-derived cells, while blue signals represent nucleated cells visualized by DAPI staining.

FIG. 2 shows a cytospin specimen of the bone marrow, which was stained with DAPI and observed under a confocal laser scanning microscope. As a result, most of the nucleated cells (blue) were visualized in green, indicating that the bone marrow cells were GFP-positive.

(2) Effect of G-CSF Administration on Myocardial Infarction Mice

At 60 days after bone marrow transplantation, the mice were intubated and anesthetized with 0.5% isoflurane gas. After thoracotomy, the left ventricle was exposed and the left coronary artery was ligated to create myocardial infarction. At 24 hours after creation of myocardial infarction, the mice were subcutaneously administered with recombinant human G-CSF (100 or 300 µg/kg/day; Chugai Pharmaceutical Co., Ltd., Japan) dissolved in physiological saline once a day for 10 consecutive days (G-CSF group). Mice in the control group received physiological saline alone.

Survival Rate

Figure 3:
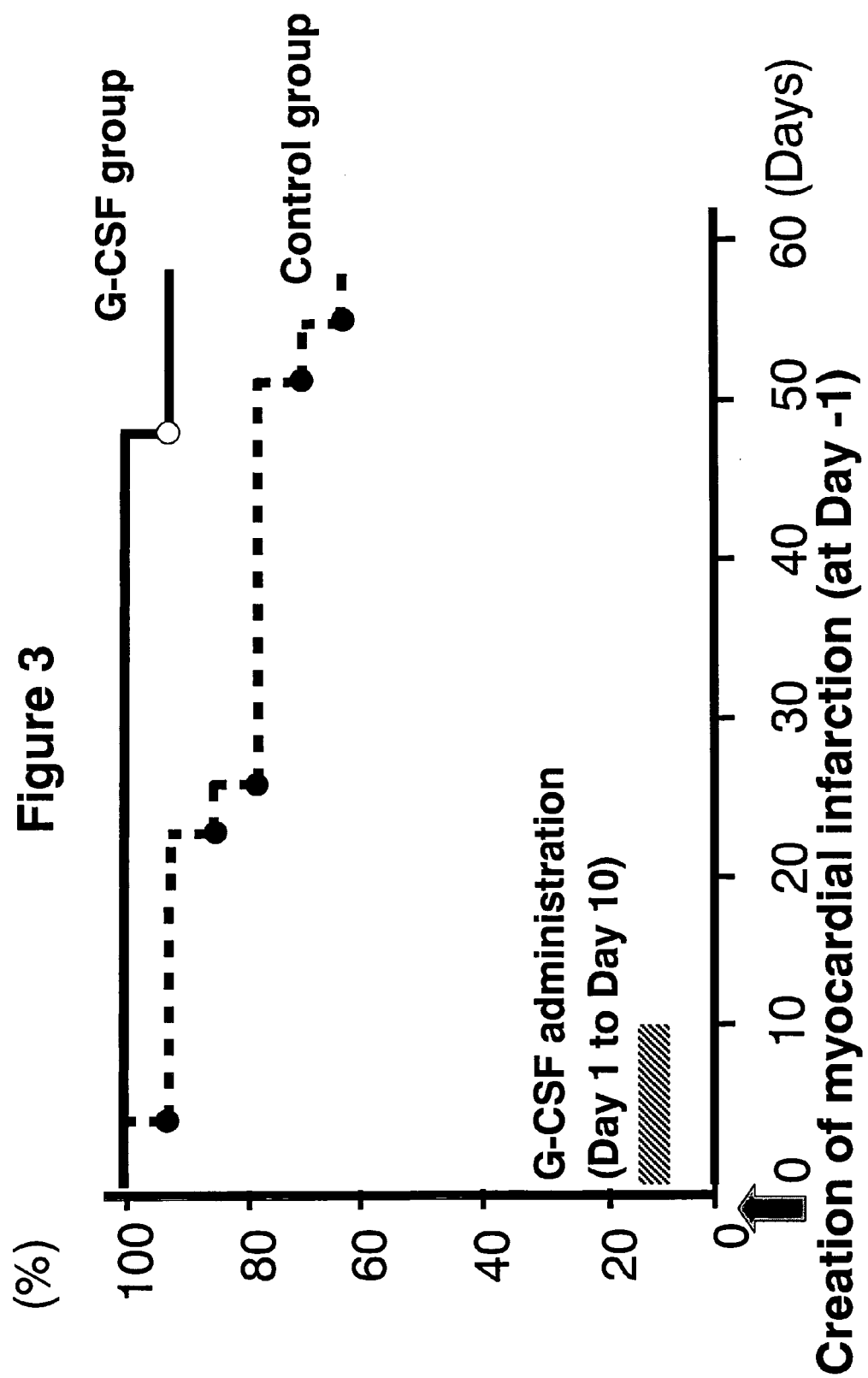
FIG. 3 shows the survival rate after creation of myocardial infarction, measured for mice administered subcutaneously with G-CSF for 10 days (G-CSF group) and mice administered with physiological saline (control group).

The survival rate was examined for both the G-CSF group (300 µg/kg) and the control group (n=68) (FIG. 3). The survival rate of the control group was about 60% at 60 days after creation of myocardial infarction, whereas the survival rate of the G-CSF group was about 90%.

Morphological Observation

Figure 4:
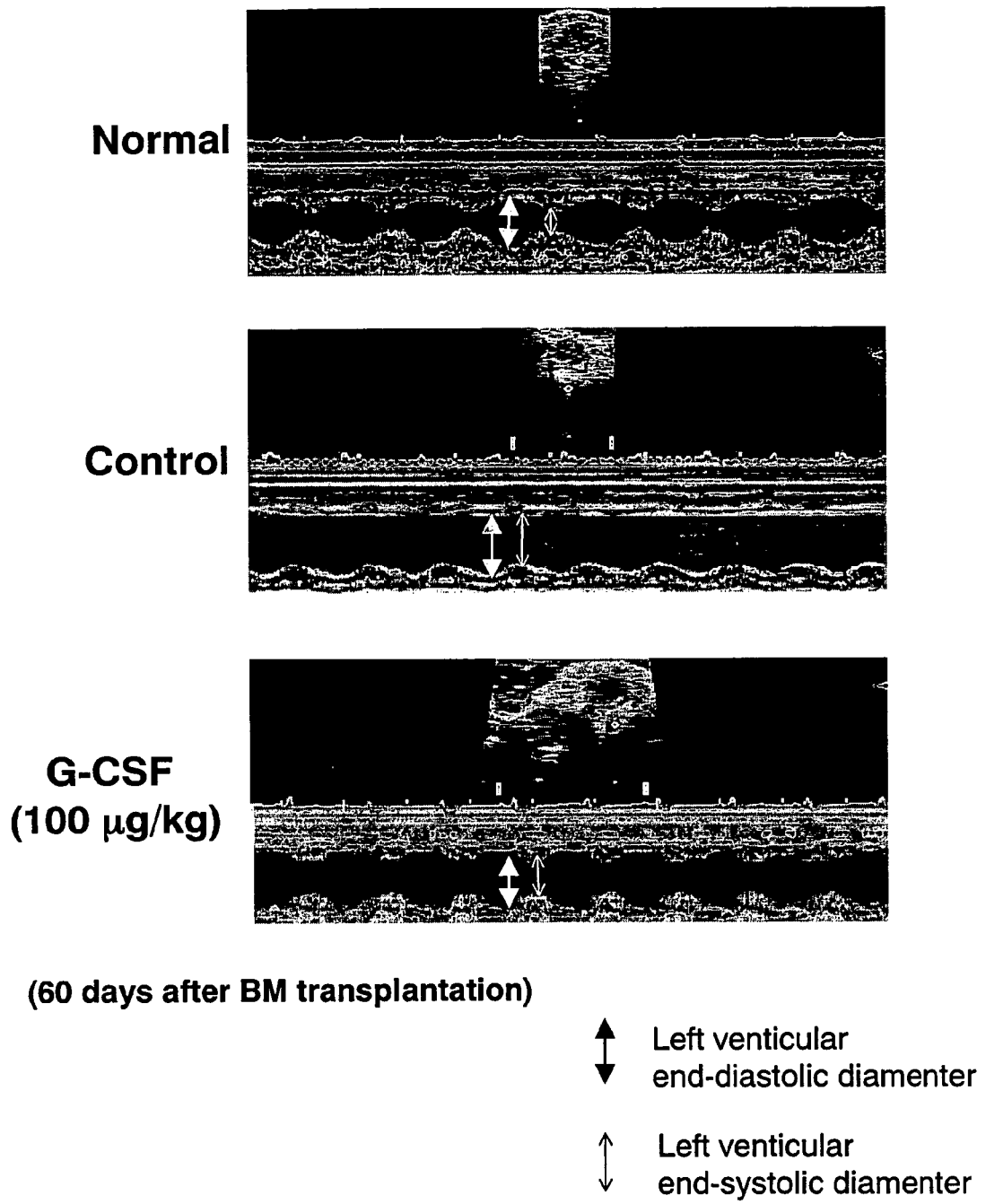
FIG. 4 shows transthoracic M-mode echocardiographic images at 60 days after creation of myocardial infarction. From the top, the panels represent the left ventricles of normal, control and G-CSF (100 µg/kg)-receiving mice, respectively.

At 60 days after creation of myocardial infarction, transthoracic echocardiography (M-mode echocardiography) was performed on normal mice and mice in the control group and in the G-CSF group by using image point 1500 ultrasonic diagnostic equipment (Philips Co., USA) provided with a 15 MHz phased array transducer, followed by morphological observation of myocardial infarct lesions. The mice were anesthetized with ketamine (30 mg/kg) and xylazine (6 mg/kg) to maintain spontaneous respiration. As shown in FIG. 4, when compared to the normal left ventricle, the control group had thinned and non-constrictive myocardium in the anterior wall, along with an increased left ventricular inner diameter. In contrast, in the G-CSF group (100 µg/kg), such an increase in the left ventricular end-diastolic diameter was prevented when compared to the control group. Moreover, the left ventricular anterior wall in the G-CSF group was low constrictive, but significantly improved when compared to the control group.

Cardiac Function

At 60 days after creation of myocardial infarction, the left ventricular end-systolic diameter (LVESD) and end-diastolic diameter (LVEDD) were determined from the M-mode images of the control group and the G-CSF group (100 or 300 µg/kg) (n=68). Their end-diastolic volume (EDV) and end-systolic volume (ESV) were also calculated by the Teichholz method. The left ventricular ejection fraction (EF) was calculated according to the following equation.

$$EF\ (\%) = [(EDV-ESV)/EDV] \times 100$$

Figure 5:
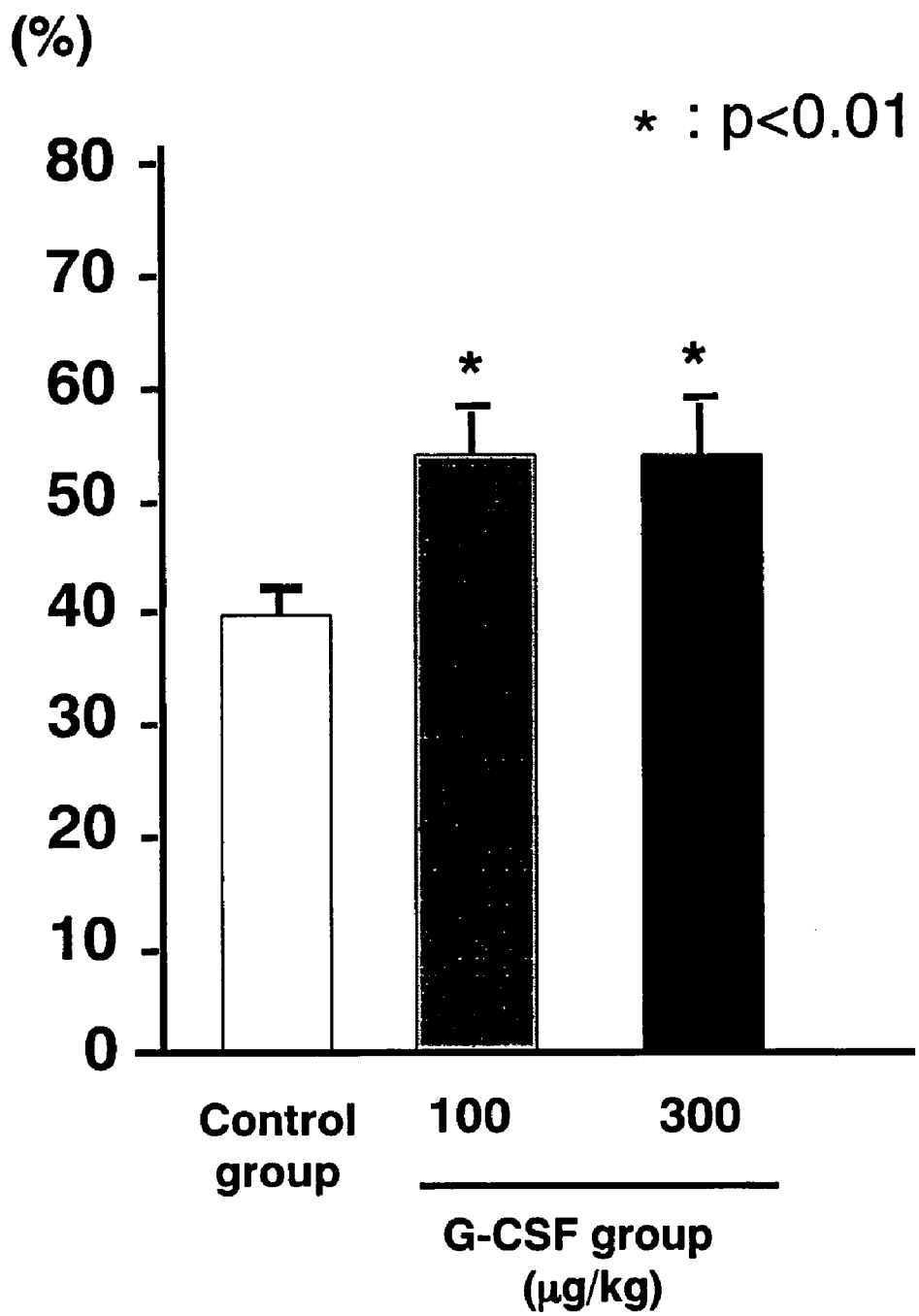
FIG. 5 is a graph showing the effect of G-CSF administration on left ventricular ejection fraction at 60 days after creation of myocardial infarction. From the left, the bars show the results of the normal group, the G-CSF group (100 µg/kg) and the G-CSF group (300 µg/kg), respectively.

The results obtained are shown in FIGS. 5 and 6. Both figures indicated that the G-CSF groups showed a significant improvement in their cardiac function.

Histological Observation (i) Preparation of Sections

The mice were anesthetized with ketamine (30 mg/kg) and xylazine (6 mg/kg). Their hearts were perfused with PBS and perfusion-fixed with 4% paraformaldehyde in PBS. The hearts were excised, embedded in OCT compound (Miles Scientific, Naperville, Ill., USA) and quickly frozen in liquid nitrogen. The embedded hearts were sliced to prepare sections.

(ii) Azan Staining

At 60 days after creation of myocardial infarction, Azan staining was performed on the frozen short-axis cross-sections of the heart left. ventricles from the control group and the G-CSF group (300 µg/kg). The results obtained are shown in FIG. 7(a). The control group showed an increase in its left ventricular diameter, along with infarct "thinning" and infarct expansion, which means so-called remodeling following myocardial infarction. In contrast, the G-CSF group showed mild post-infarction remodeling, and infarct "thinning" and infarct expansion were reduced. This indicated that G-CSF administration allowed tissue regeneration in myocardial infarct lesions and hence prevented remodeling.

Furthermore, the sections from the G-CSF group were observed under a confocal laser scanning microscope, indicating that a large number of GFP-positive bone marrow cells were infiltrated into myocardial infarct lesions (FIG. 7(b), right panel).

(iii) Immunostaining

The frozen sections (6 µm) were rinsed with PBS and stained overnight at 4° C. using a specific antibody. The sections were then rinsed three times with PBS and incubated with a TRITC (DAKO, Japan)-conjugated secondary antibody at 4° C. for 4 hours (red). The nuclei were stained with DAPI (Sigma Aldrich) (blue).

Figure 8:
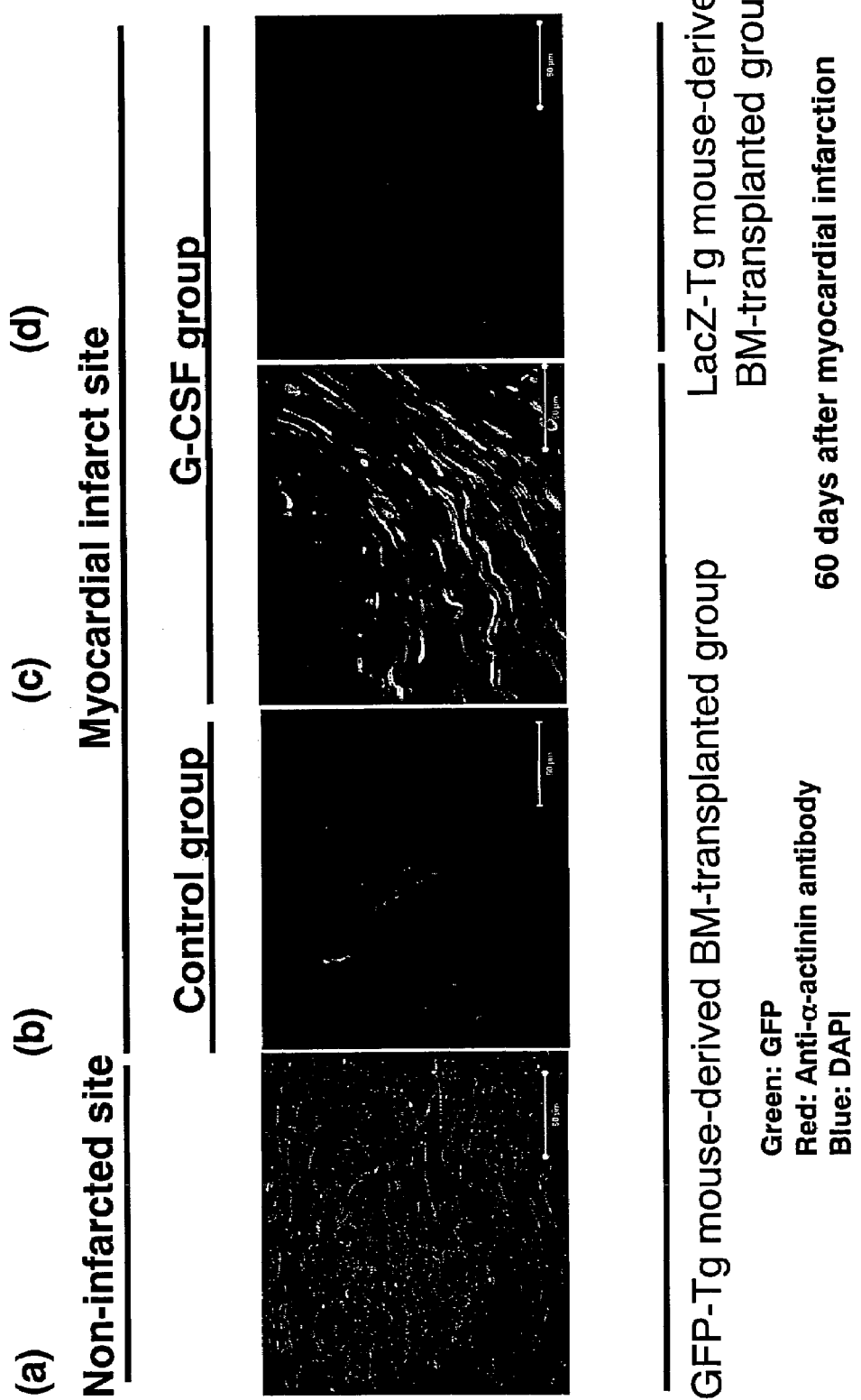
FIGS. 8(a)-8(d) shows confocal laser scanning microscopic photographs of myocardial infarct lesions as follows: (a) non-infarcted site; (b) myocardial infarct lesion in the control group; (c) myocardial infarct lesion in the G-CSF group (100 μg/kg); and (d) myocardial infarct lesion in Lac-Z transgenic mice administered with G-CSF (100 μg/kg).
Figure 9:
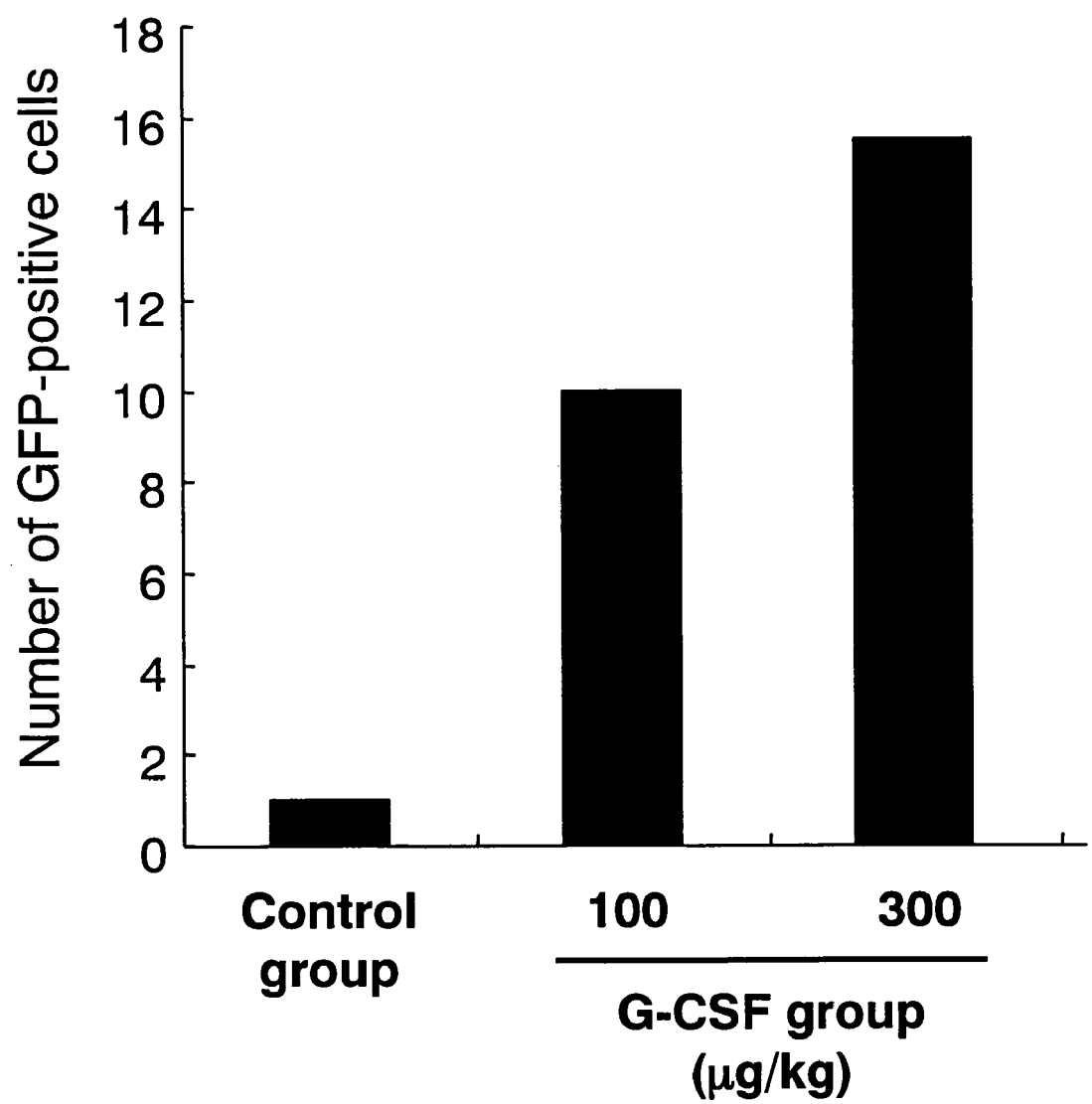
FIG. 9 is a graph showing the number of GFP-positive cells present in myocardial infarct lesions.

Myocardial infarct lesions were observed under a confocal laser scanning microscope (LSM410; Carl Zeiss, Jena, Germany) (FIG. 8). The sections of non-infarcted sites were stained with anti-α-actinin antibody (clone EA-53; Sigma Aldrich, Saint Louis, Mo., USA). Myocardial cells were stained in red and a few GFP-positive cells remained within the blood vessels (a). The control group only showed a few GFP-positive cells in its infarct lesions (b). In contrast, the G-CSF group (300 μg/kg) showed a large number of GFP-positive cells in its infarct lesions (c). Using Lac-Z transgenic mice (10-12 weeks of age; Jackson Laboratories, Bar Harbor, Me., USA) as donor mice, the same experiment as used for (c) was repeated to confirm that the green fluorescence observed in the infarct lesions of (c) was not non-specific fluorescence (d). In addition, images obtained with the confocal laser scanning microscope were transferred to a computer and analyzed with NIH image software. The number of GFP-positive cells was calculated relative to the number per unit area of cells present in infarct lesions of each group. The results obtained are shown in FIG. 9. It was indicated that upon G-CSF administration, bone marrow-derived cells migrated to myocardial infarct lesions.

Next, a further experiment was performed to confirm what type of cells these GFP-positive cells were.

FIG. 10 shows the results of immunostaining with anti-α-smooth muscle actin antibody (clone 1A4; Sigma Aldrich). The bone marrow-derived GFP-positive cells were stained in red, indicating that they were differentiated into smooth muscle cells.

Figure 11:
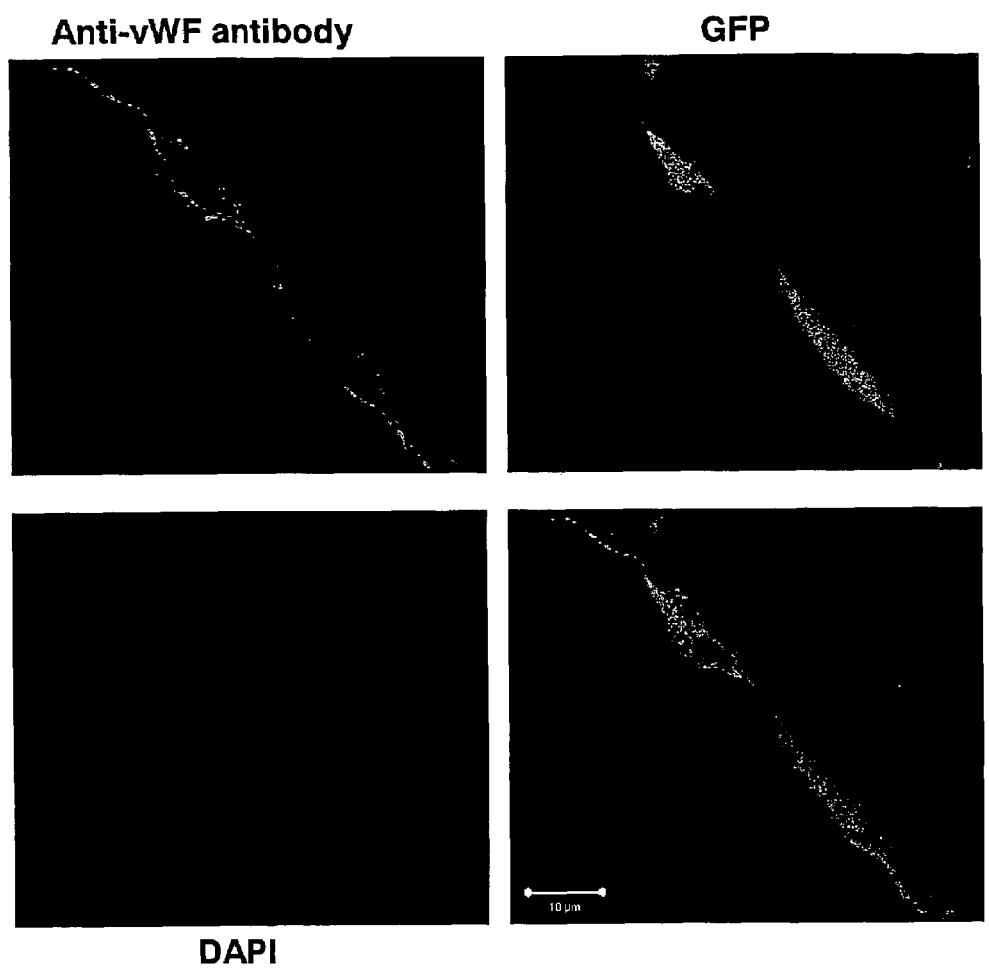
FIG. 11 shows confocal laser scanning microscopic photographs of a single myocardial infarct lesion immunostained with anti-von Willebrand factor (vWF) antibody. Green signals represent GFP-positive cells, blue signals represent DAPI-stained nuclei, and red signals represent vWF.

Next, to study the cells for von Willebrand factor (vWF) which was an endothelial cell marker, immunostaining was performed with anti-vWF antibody (clone F8/86; DAKO) (FIG. 11). The results showed areas in which GFP signals were surrounded by vWF signals, indicating that the GFP-positive cells were also differentiated into endothelial cells.

Figure 12:
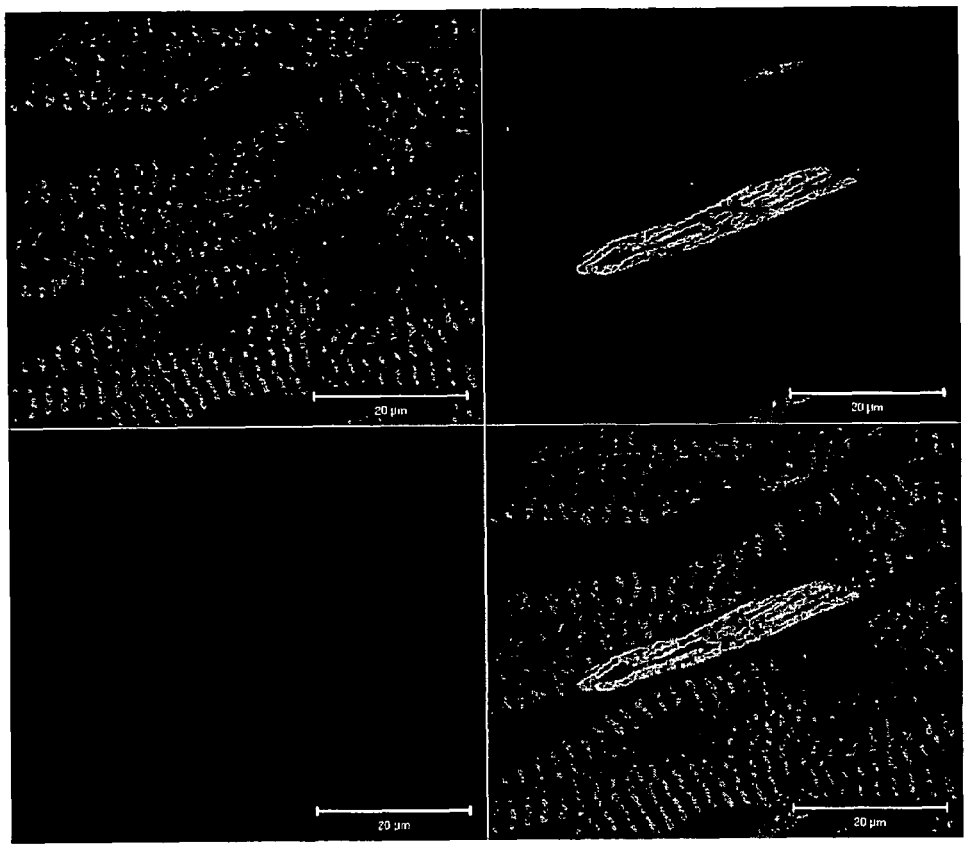
FIG. 12 shows microscopic photographs of a single myocardial infarct lesion immunostained with anti-actinin antibody. Green signals represent GFP-positive cells, blue signals represent DAPI-stained nuclei, and red signals represent actinin.
Figure 13:
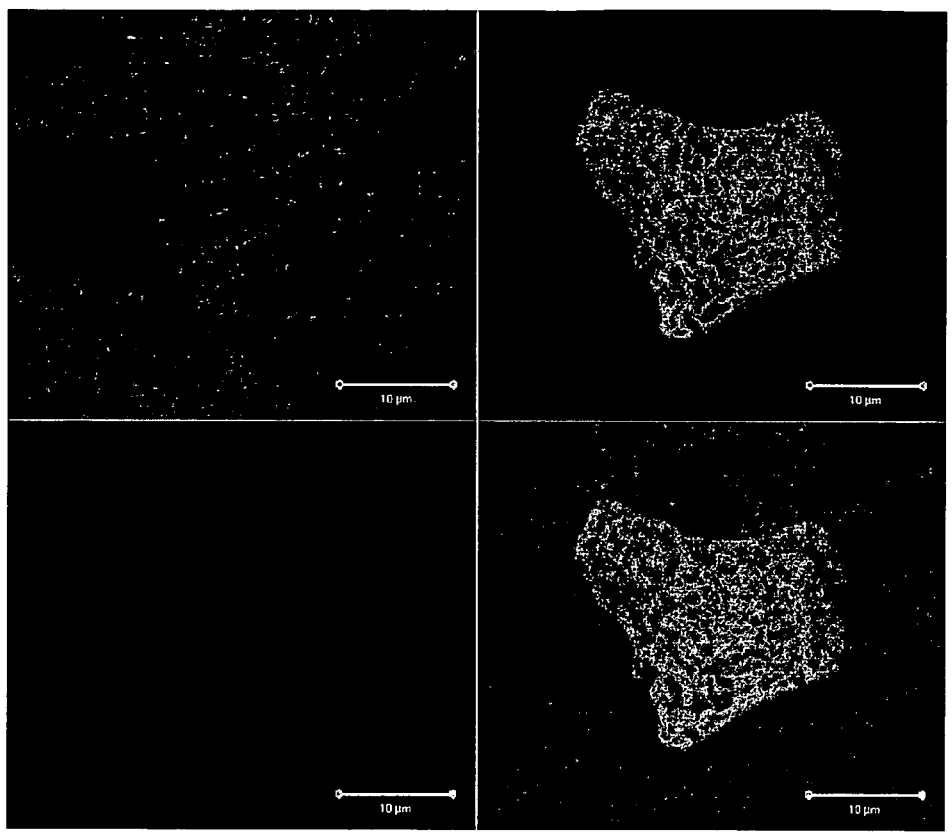
FIG. 13 shows microscopic photographs of a single myocardial infarct lesion immunostained with anti-actinin antibody. Green signals represent GFP-positive cells, blue signals represent DAPI-stained nuclei, and red signals represent actinin.
Figure 14:
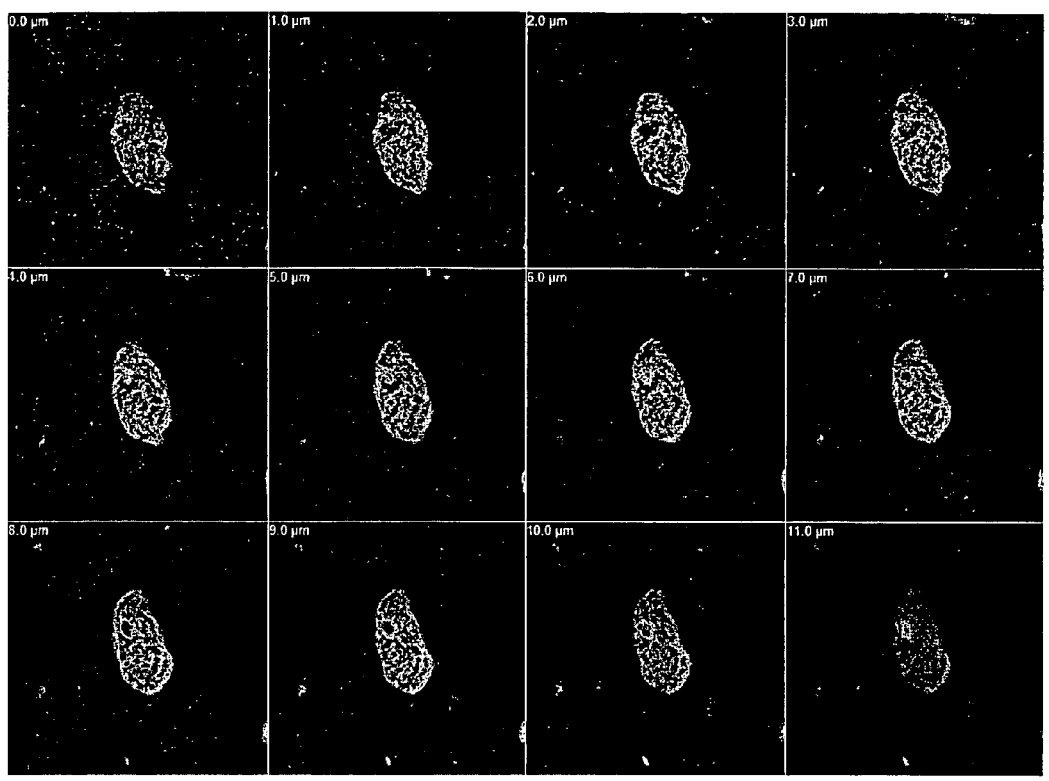
FIG. 14 shows microscopic photographs of a single myocardial infarct lesion sliced in 1 μm sections and immunostained with anti-actinin antibody. Green signals represent GFP-positive cells, blue signals represent DAPI-stained nuclei, and red signals represent actinin.

Further, myocardial cells were immunostained with anti-α-actinin antibody (FIGS. 12 to 14). As shown in FIGS. 12 and 13, actinin-positive signals were observed among GFP-positive cells, some of which showed a cross striation pattern and were suggested to be myocardial cells. Myocardium having a perfect cross striation pattern was regenerated from GFP-positive cells. FIG. 14 shows photographs of sections sliced in 1 μm increments. The results indicated that bone marrow-derived GFP-positive cells achieved complete regeneration of myocardial cells.

Figure 15:
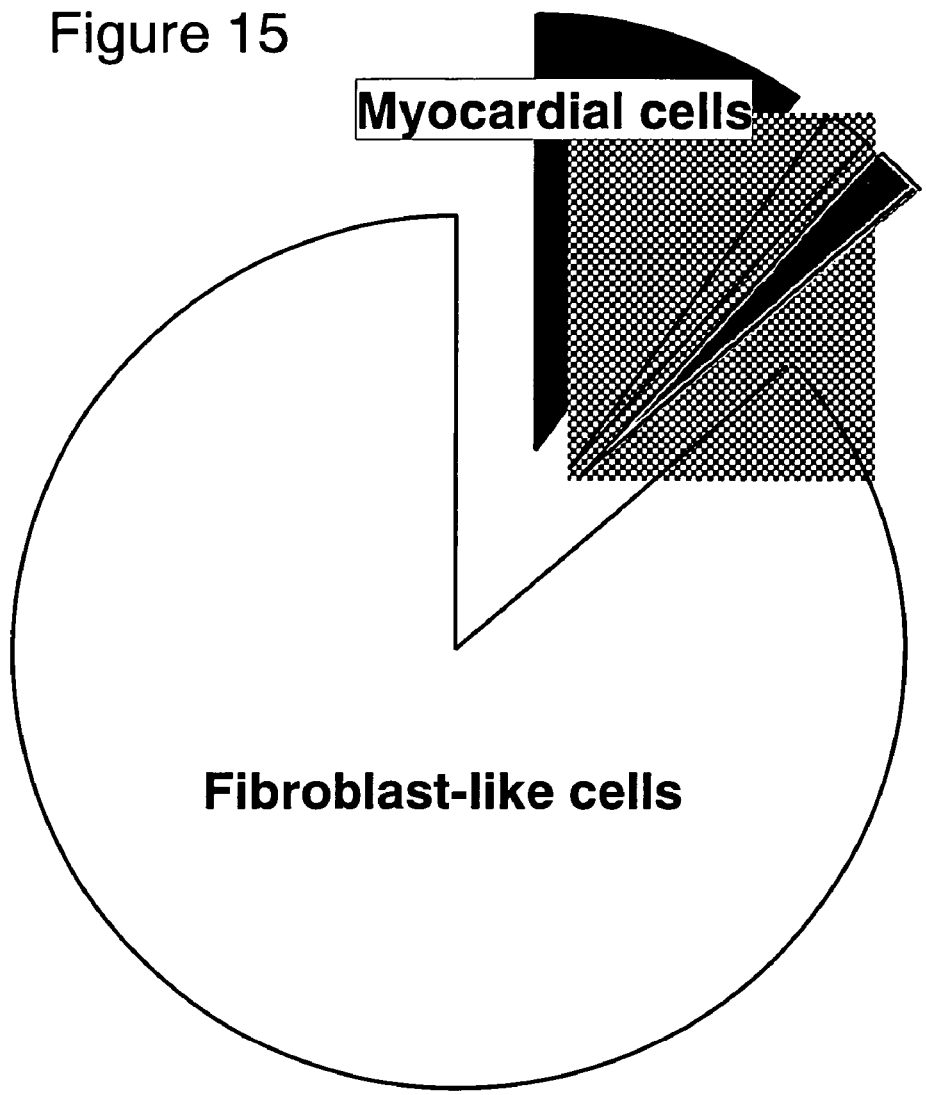
FIG. 15 is a graph showing percentages of GFP-positive cells by type in myocardial infarct lesions after G-CSF administration.

FIG. 15 summarizes the percentages of myocardial cells, vascular endothelial cells, smooth muscle cells and fibroblasts among GFP-positive cells observed in myocardial infarct lesions at 60 days after creation of myocardial infarction. The number of cells was determined as follows. Each heart was divided into three parts, i.e., apex, middle and base, and the volume of infarcted tissue was calculated from the area of GFP-positive cells and the tissue thickness in each part. The number of GFP-positive cells per unit area was counted to determine the density of GFP-positive cells. The density of GFP-positive cells and the infarct volume were used to calculate the number of GFP-positive cells in the infarcted tissue. At least 80% of the cells were spindle-shaped and had different morphology than hematopoietic cells. Moreover, these cells were also found to be CD45-negative and Mac-1-negative. This indicated that fibroblasts were the largest in number among GFP-positive cells present in myocardial infarct lesions.

Example 2

Transplantation of Bone Marrow-derived Single Hematopoietic Stem Cells

Figure 16:
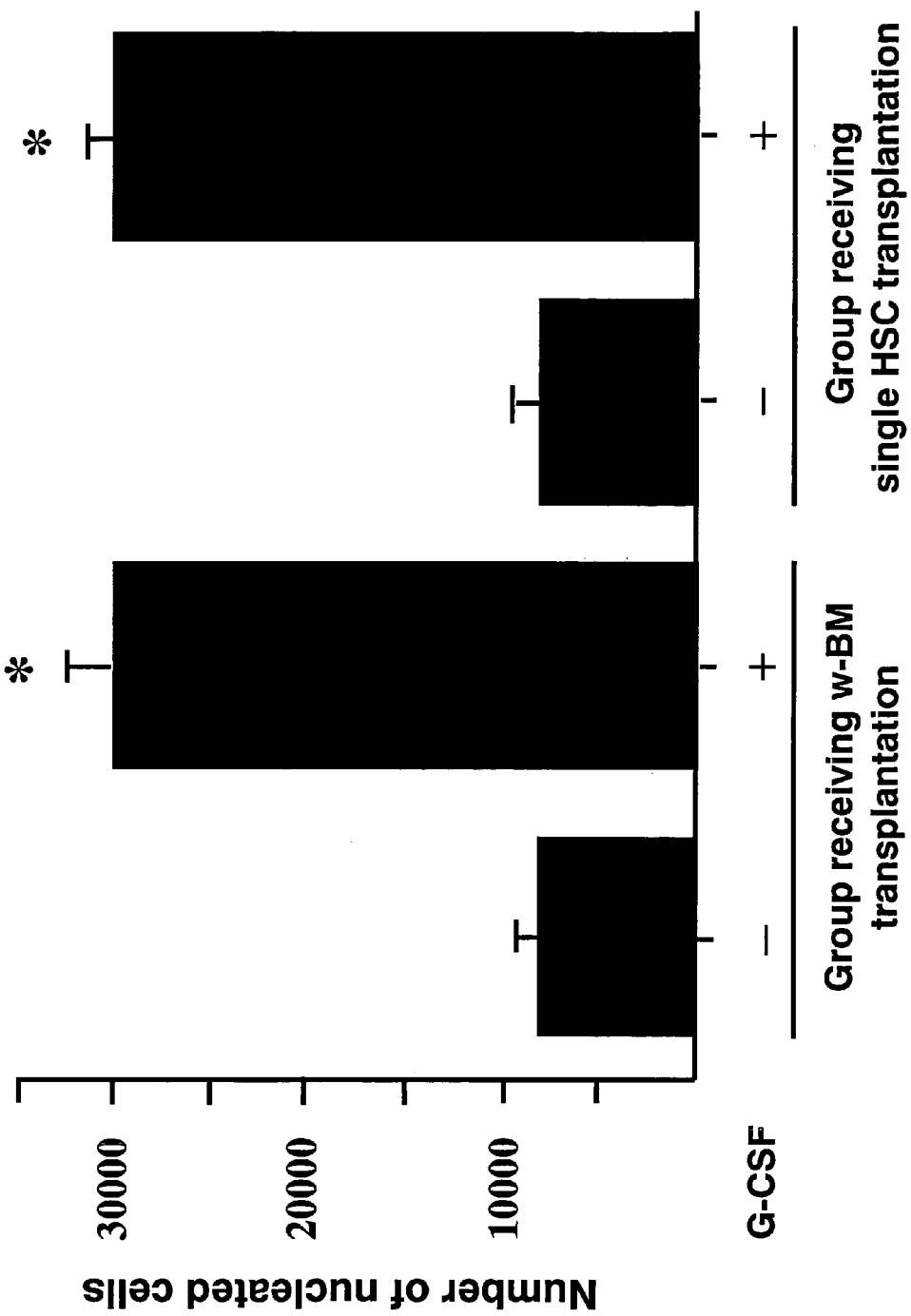
FIG. 16 is a graph showing the effect of G-CSF administration on the number of peripheral blood nucleated cells in both the group receiving whole bone marrow transplantation and the group receiving single hematopoietic stem cell transplantation.

Bone marrow was collected from GFP transgenic mice and a GFP-positive fraction was separated with a cell sortor, followed by collection of c-kit-positive, Sca-1-positive, linage antigen-negative and CD34-negative hematopoietic stem cells. A single cell selected from these cells and $5 \times 10^6$ cells of a bone marrow crude fraction collected from another normal donor mouse were transplanted into the bone marrow of lethally irradiated recipient mice. After 3 months, the rate of GFP-positive cells engrafted in the bone marrow was confirmed. After thoracotomy under anesthesia, the left coronary artery was ligated to create myocardial infarction. The mice were then subcutaneously administered with G-CSF (300 μg/kg) for 10 days. The number of peripheral blood nucleated cells at 10 days after G-CSF administration was about 30,000 in both the group receiving whole bone marrow transplantation and the group receiving single hematopoietic stem cell transplantation; there was no difference between these two groups (FIG. 16).

Figure 17:
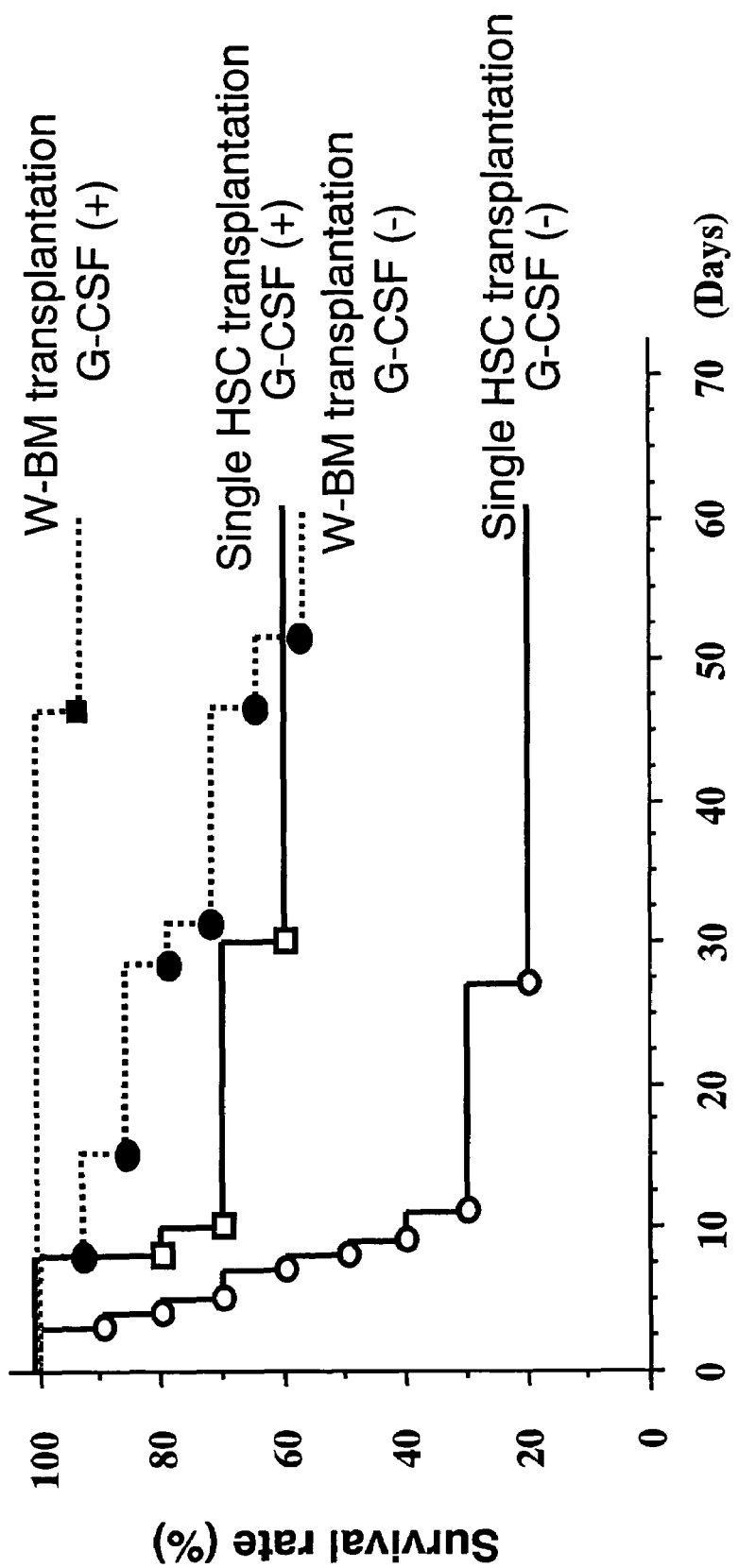
FIG. 17 is a view showing the effect of G-CSF administration on survival rate after creation of myocardial infarction. In the figure, the dotted line represents the group receiving whole bone marrow transplantation, the solid line represents the group receiving single hematopoietic stem cell transplantation, solid and open squares represent the group treated with G-CSF (+), and open and solid circles represent the group untreated with G-CSF (−).

The survival rate was examined for both the group receiving single hematopoietic stem cell transplantation (solid line) and the group receiving whole bone marrow transplantation (dotted line) when administered with (square) or without (circle) G-CSF (FIG. 17). Not only the group receiving whole bone marrow transplantation, but also the group receiving single hematopoietic stem cell transplantation showed a significant improvement in their survival rate upon G-CSF administration.

Figure 18:
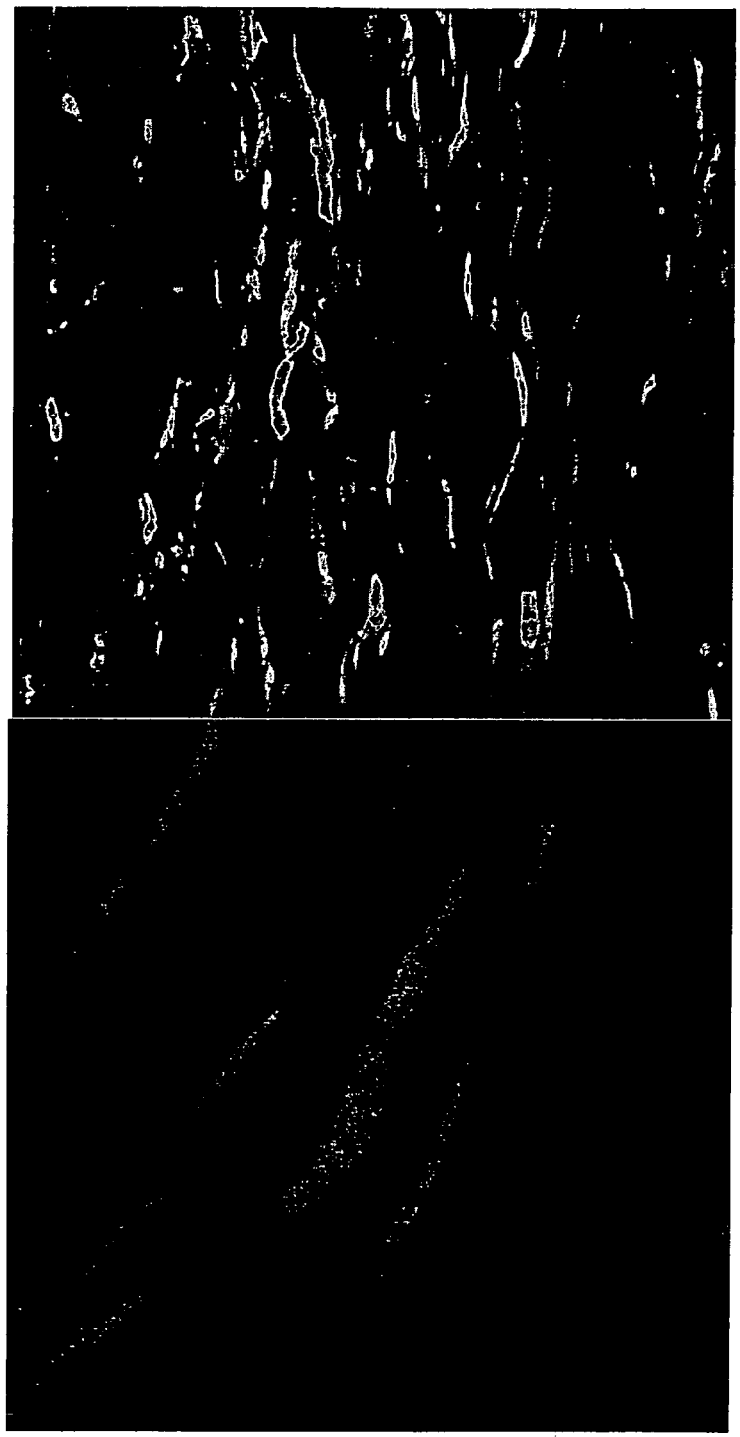
FIG. 18 shows confocal laser scanning microscopic photographs of myocardial infarct lesions immunostained with anti-vimentin antibody in the group receiving single hematopoietic stem cell transplantation. Green signals represent GFP-positive cells, blue signals represent DAPI-stained nuclei, and red signals represent vimentin.

Next, the same procedure as used in Example 1 was repeated to prepare sections of myocardial infarct lesions from the group receiving single hematopoietic stem cell transplantation, followed by immunostaining with anti-vimentin antibody (PROGEN BIOTECHNIK GMBH, Cat. No. GP53). As shown in FIG. 18, the presence of GFP-positive cells was observed in myocardial infarct lesions. The results indicated that a single GFP-positive hematopoietic stem cell was engrafted in a myocardial infarct lesion. Moreover, this cell was found to be stained with anti-vimentin antibody, confirming that it was differentiated into a fibroblast.

Figure 19:
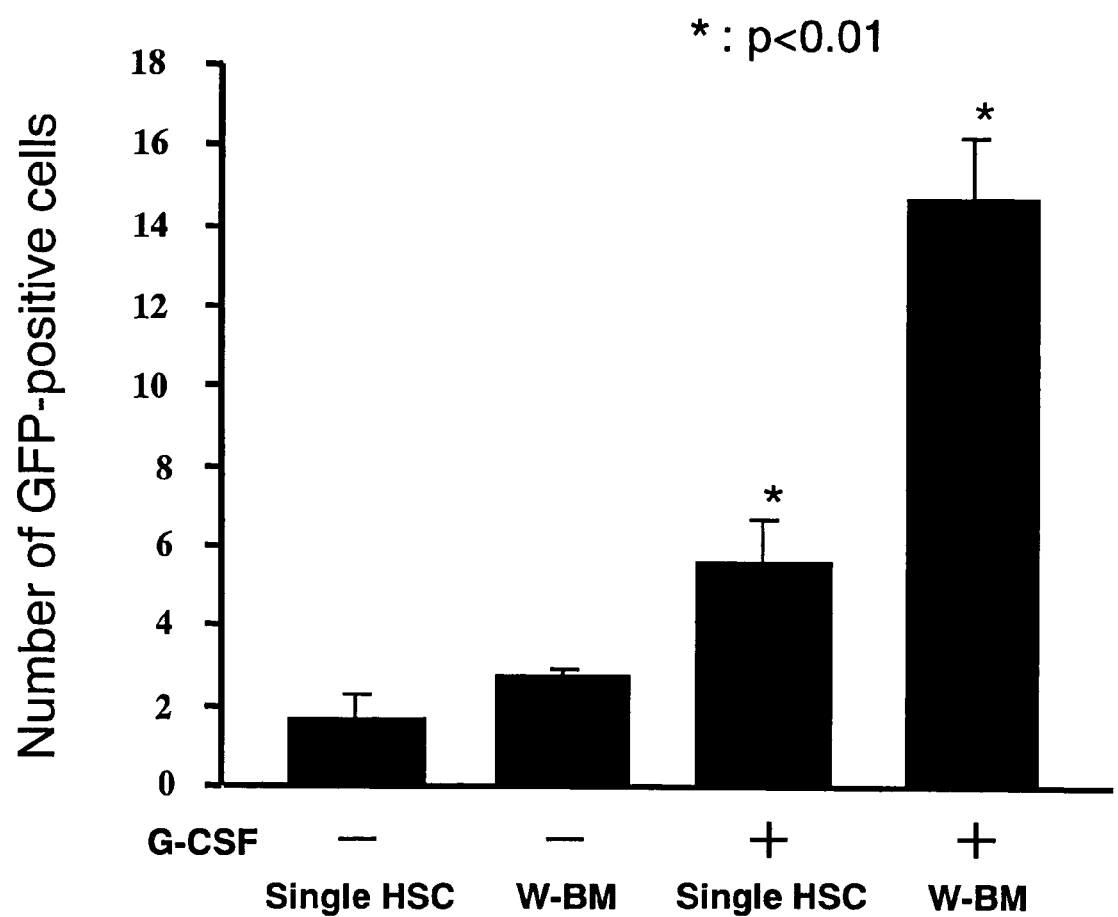
FIG. 19 is a graph showing the effect of G-CSF administration on the number of GFP-positive cells in both the group receiving whole bone marrow transplantation and the group receiving single hematopoietic stem cell transplantation.

Further, the same procedure as used in Example 1 was repeated to determine the number of GFP-positive cells in both the group receiving single hematopoietic stem cell transplantation and the group receiving whole bone marrow transplantation when administered with or without G-CSF (FIG. 19). Not only the group receiving whole bone marrow transplantation, but also the group receiving single hematopoietic stem cell transplantation showed a significant increase in the number of GFP-positive cells upon G-CSF administration.

Figure 20:
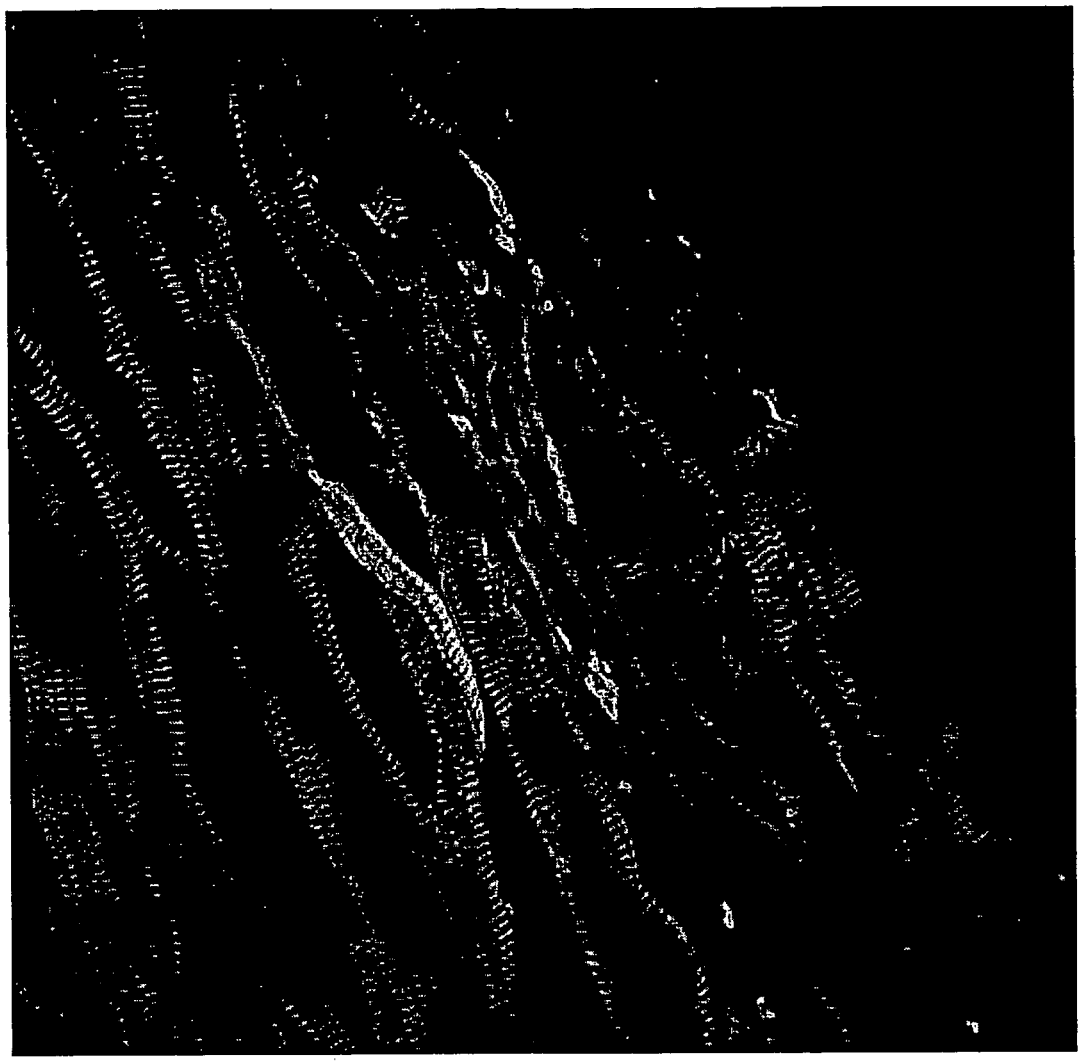
FIG. 20 is a confocal laser scanning microscopic photograph showing the boundary area of myocardial infarction, immunostained with anti-actinin antibody, in the group receiving single hematopoietic stem cell transplantation when administered with G-CSF. Green signals represent GFP-positive cells, blue signals represent DAPI-stained nuclei, and red signals represent actinin.

Immunostaining with anti-myocardial actinin antibody was performed on left ventricular sections from the group receiving single hematopoietic stem cell transplantation when administered with G-CSF (FIG. 20). GFP-positive cells were found to be actinin-positive, indicating that they were differentiated into myocardial cells.

In Examples 1 and 2 above, all values were expressed as mean±SEM. Statistical significance between means was calculated by ANOVA. Comparison between the control group and the G-CSF group was made by log-rank assay or nonparametric Fisher's multiple comparison test. p<0.05 was considered as statistically significant.

Example 3

Lethally irradiated C57BL/6 mice (8-10 weeks of age) were transplanted through their tail veins with whole bone marrow cells (w-BM) collected from the bone marrow of CAG-EGFP mice (Okabe M. et al., FEBS Lett. 1997, 407: 313-319) or with c-kit-positive, Sca-1-positive and lineage antigen-negative single population cells (KSL-SP). After 8 weeks, the left coronary artery was ligated to create myocardial infarction (MI) in each mouse. At 24 hours after MI creation, the mice were subcutaneously administered with physiological saline (G-CSF(−)) or 300 μg/kg/day G-CSF (G-CSF(+)) once a day for 10 consecutive days. At 8 weeks after MI creation, the mice were dissected and their hearts were analyzed immunohistologically. For each mouse group (n=10), 100 sample specimens were counted for the numbers of GFP-positive cells, GFP-positive and vimentin-positive cells, as well as GFP-positive and actinin-positive cells in infarct lesions. Table 1 shows average numbers of these GFP-positive cells.

TABLE 1

Quantitative analysis of GFP-positive cells in infarct lesions

| Mouse | GFP-positive cells | | |
|---|---|---|---|
| | Total* | Vimentin positive | Actinin positive |
| w-BM G-CSF (−) | 8841 | 1813 | 65 |
| w-BM G-CSF (+) | 119802 | 37457 | 5403 |
| KSL-SP G-CSF (−) | 1224 | 480 | 0 |
| KSL-SP G-CSF (+) | 41779 | 9322 | 3 |

*Total number of GFP-positive cells in infarct lesions

In the w-BM groups, both vimentin-positive cells (fibroblasts) and actin-positive cells (myocardial cells) were regenerated from the whole bone marrow, whereas in the KSL-SP groups, only fibroblasts were regenerated. This result suggests that myocardial cells are not regenerated from hematopoietic stem cells. Myocardial cell regeneration is considered to be mediated by differentiation from stem cells of the mesenchymal lineage.

Next, when attention is directed to the effect of G-CSF, G-CSF was found to recruit fibroblasts and myocardial cells in the w-BM group. In the KSL-SP group, G-CSF was found to recruit fibroblasts, but only three myocardial cells were observed in this group. These myocardial cells probably appear to be a result of cell fusion, but not regeneration.

In all the groups, as shown in FIG. 17, G-CSF administration provides an improvement in survival rate. These effects are mediated by recruitment of fibroblasts and myocardial cells in the w-BM group, whereas they are mediated by recruitment of fibroblasts in the KSL-SP group. In particular, an increase in the number of fibroblasts contributes to wound healing at myocardial infarct sites and facilitates the prevention of remodeling known to be correlated with mortality.

INDUSTRIAL APPLICABILITY

Simply by using the substance for fibroblast recruitment according to the present invention to induce migration of a few bone marrow-derived cells, it is possible to regenerate tissues such as myocardial infarct lesions and improve the survival rate without performing fibroblast transplantation. Moreover, the use of the therapeutic agent for wound healing according to the present invention enables a strong healing of wounded sites.

The invention claimed is:

1. A method for recruiting fibroblast into a heart in need thereof, which comprises administering granulocyte colony-stimulating factor (G-CSF) in an amount sufficient by itself to recruit fibroblast into said heart.

2. The method according to claim 1, wherein the heart is a heart after the onset of heart disease.

3. The method according to claim 2, wherein the heart disease is myocardial infarction.

4. A method according to claim 1, wherein said G-CSF is administered to a mammal.

5. A method according to claim 1, wherein said G-CSF is administered to a human.

6. A method according to claim 1, wherein said G-CSF is administered by injection in a dosage form suitable for injection.

7. The method according to claim 4, wherein the G-CSF is mammalian G-CSF.

8. The method according to claim 5, wherein the G-CSF is in a purified form.

9. The method of claim 5, wherein the G-CSF is conjugated with polyethylene glycol or vitamin B12.

10. The method of claim 5, wherein the G-CSF is recombinant G-CSF.

11. The method of claim 5, wherein said sufficient amount falls within the range of 1-50 μg/kg/day per adult human.

* * * * *